(12) United States Patent
Hsu et al.

(10) Patent No.: US 9,950,995 B2
(45) Date of Patent: Apr. 24, 2018

(54) CRYSTAL FORMS OF VERAPAMIL HYDROCHLORIDE

(71) Applicant: Center Laboratories, Inc., Taipei (TW)

(72) Inventors: Jui-Pao Hsu, Taipei (TW); Guang-Tzuu Shane, Taipei (TW); Yu-Yin Yeh, Taipei (TW); Meng-Ju Lee, Taipei (TW)

( * ) Notice: Subject to any disclaimer, the term of this patent is extended or adjusted under 35 U.S.C. 154(b) by 0 days.

(21) Appl. No.: 15/521,304

(22) PCT Filed: Jul. 13, 2015

(86) PCT No.: PCT/CN2015/083854
§ 371 (c)(1),
(2) Date: Apr. 24, 2017

(87) PCT Pub. No.: WO2016/065930
PCT Pub. Date: May 6, 2016

(65) Prior Publication Data
US 2017/0305841 A1    Oct. 26, 2017

Related U.S. Application Data

(60) Provisional application No. 62/072,172, filed on Oct. 29, 2014.

(51) Int. Cl.
C07C 255/00 (2006.01)
C07C 255/43 (2006.01)
C07C 253/34 (2006.01)

(52) U.S. Cl.
CPC .......... *C07C 255/43* (2013.01); *C07C 253/34* (2013.01); *C07B 2200/13* (2013.01)

(58) Field of Classification Search
CPC .... C07C 255/00; C07C 255/43; C07C 253/34
See application file for complete search history.

(56) References Cited

FOREIGN PATENT DOCUMENTS

| CN | 101012185 | * | 8/2007 |
| DE | 3723684 | * | 1/1989 |
| PL | 162512 | * | 12/1993 |

OTHER PUBLICATIONS

DE3723684, abstract, 1989, caplus an 1989:439017.*
PL162512, abstract, 1995, caplus an 1995:328623.*

* cited by examiner

*Primary Examiner* — Sun Jae Yoo

(57) ABSTRACT

Novel crystal forms of (R)-(−)-verapamil hydrochloride are disclosed.

5 Claims, 3 Drawing Sheets

CRYSTAL FORMS OF VERAPAMIL HYDROCHLORIDE

BACKGROUND

1. Field of the Present Disclosure

The present disclosure relates to novel crystalline forms of (R)-(+) Verapamil hydrochloride.

2. Description of Related Art

Verapamil HCl (e.g., 2-(3,4-dimethoxyphenyl)-5-[2-(3,4-dimethoxyphenyl)ethyl-methylamino]-2-propan-2-ylpentanenitrile) is a known drug with various medicinal indications. Traditionally, it is used for treating coronary disease, such as hypertension. The compound has a stereogenic center, hence can be separated into its optical enantiomers. The (S)-enantiomer is known to possess the majority of the calcium channel antagonist activity, whereas the (R)-enantiomer is known to possess agonist activity toward somatostatin receptor 2, and antagonist activity toward orexin receptors 1 and 2, dopamine $D_{2L}$ receptor, sodium and calcium channels; accordingly, the (R)-enantiomer is useful as a medicament for treating diseases or conditions related to these receptors in a human subject. Therefore, single isomer products may offer clinical utility on medical conditions related to those receptors and/or ion channels.

Further, in the production of drug substance for use as a medicine, it is advantageous to prepare the drug substance in crystal form, for crystals are easier to handle while exhibiting improved properties, such as solubility, stability, and pharmacokinetics.

SUMMARY

The following presents a simplified summary of the disclosure in order to provide a basic understanding to the reader. This summary is not an extensive overview of the disclosure and it does not identify key/critical elements of the present disclosure or delineate the scope of the present disclosure. Its sole purpose is to present some concepts disclosed herein in a simplified form as a prelude to the more detailed description that is presented later.

The object of the present disclosure is to provide novel crystals of (R)-(+) verapamil hydrochloride. After intensive studies, form E and form T crystals of (R)-(+) verapamil hydrochloride are obtained. Each crystals has improved storage stability, solubility and/or purity, and is easier to process under typical pharmaceutical processing conditions such as wet granulation, thus the (R)-(+) verapamil hydrochloride crystalline of the present disclosure is suitable for use as a drug substance or an active compound of a pharmaceutical composition.

Accordingly, it is the first objective of the present disclosure to provide a form E crystalline of (R)-(+) verapamil hydrochloride, which yields a powder X-ray diffraction pattern comprising characteristic peaks of 12.7°±0.1°, 18.7°±0.1°, 19.2°±0.1°, 20.2°±0.1°, and 21.2°±0.1° at reflection angles 2θ. According to a further example, the powder X-ray diffraction pattern of form E crystalline of (R)-(+) verapamil hydrochloride further comprises characteristic peaks of 6.4°±0.1°, 8.3°±0.1°, 10.7°±0.1°, 15.5°±0.1°, 15.9°±0.1°, 17.5°±0.1°, 20.4°±0.1°, 23.9°±0.1°, 24.4°±0.1°, 25.4°±0.1°, 25.9°±0.1°, 27.7°±0.1°, 27.0°±0.1°, and 29.8°±0.1° at reflection angles 2θ. Specifically, it yields a powder X-ray diffraction pattern as depicted in FIG. 2. The form E crystalline, as measured by differential scanning calorimetry (DSC), exhibits an endothermic peak at about 139±0.1° C. Further, it has a water content of about 0% (wt %) at 3% relative humidity (RH), and a water content of about 21% (wt %) at 95% RH.

The second aspect of the present disclosure is to provide a form T crystal of (R)-(+) verapamil hydrochloride, which yields a powder X-ray diffraction pattern comprising characteristic peaks of 8.5°±0.1°, 9.5°±0.1°, 17.6°±0.1°, 21.4°±0.1°, and 22.3°±0.1° at reflection angles 2θ. According to a further example, the powder X-ray diffraction pattern of form T crystalline of (R)-(+) verapamil hydrochloride further comprises characteristic peaks of 5.4°±0.1°, 9.6°±0.1°, 15.7°±0.1°, 17.1°±0.1°, 21.5°±0.1°, 21.6°±0.1°, 23.3°±0.1°, 24.6°±0.1° and 25.5°±0.1° at reflection angles 2θ. Specifically, it yields a powder X-ray diffraction pattern as depicted in FIG. 3. The form T crystalline, as measured by DSC, exhibits an endothermic peak at about 132±0.1° C. Further, the form T crystal has a water content of about 0 (wt %) at 3% RH, and a water content of about 23% (wt %) at 95% RH.

Preferably, each crystals of (R)-(+) verapamil hydrochloride is substantially pure, with a level of individual impurity that is less than 1.0%; preferably, less than 0.5%; and most preferably, less than 0.1%. Accordingly, the form E or T crystalline of (R)-(+) verapamil hydrochloride is suitable for use as a drug substance for manufacturing a medicament. The medicament is suitable for treating diseases or conditions related to orexin receptor 1, orexin receptor 2, somatostatin receptor 2, dopamine $D_{2L}$ receptor, sodium channel or L- and N-type calcium channels in a subject.

The third aspect of the present disclosure is directed to a method of making a crystalline of (R)-(+)-verapamil hydrochloride, which comprises steps of, dissolving (R)-(+)-verapamil hydrochloride in the least amount of a solvent to form a solution; cooling the solution; and collecting an amount of precipitates of the crystalline of (R)-(+)-verapamil hydrochloride from the solution, wherein the collected precipitate is the crystalline of (R)-(+)-verapamil hydrochloride, which has a powder X-ray diffraction pattern comprising either characteristic peaks of 8.5°±0.1°, 9.5°±0.1°, 17.6°±0.1°, 21.4°±0.1°, and 22.3°±0.1° at reflection angles 2θ; or characteristic peaks of 12.7°±0.1°, 18.7°±0.1°, 19.2°±0.1°, 20.2°±0.1°, and 21.2°±0.1° at reflection angles 2θ.

According to embodiments of the present disclosure, the dissolving step is performed at an elevated temperature that is between about 53° C. and 70° C. In one example, (R)-(+)-verapamil hydrochloride is dissolved at about 60° C. In another example, (R)-(+)-verapamil hydrochloride is dissolved at about 70° C.

According to some embodiments of the present disclosure, the cooling step is performed by cooling the solution to about room temperature. In other embodiments, the cooling step is performed by cooling the solution to about 4° C.

Optionally, the method of the present disclosure may further comprise a step of drying the precipitates.

Still optionally, the method of the present disclosure may further comprise a step of heating the solvent.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

Figure 1:
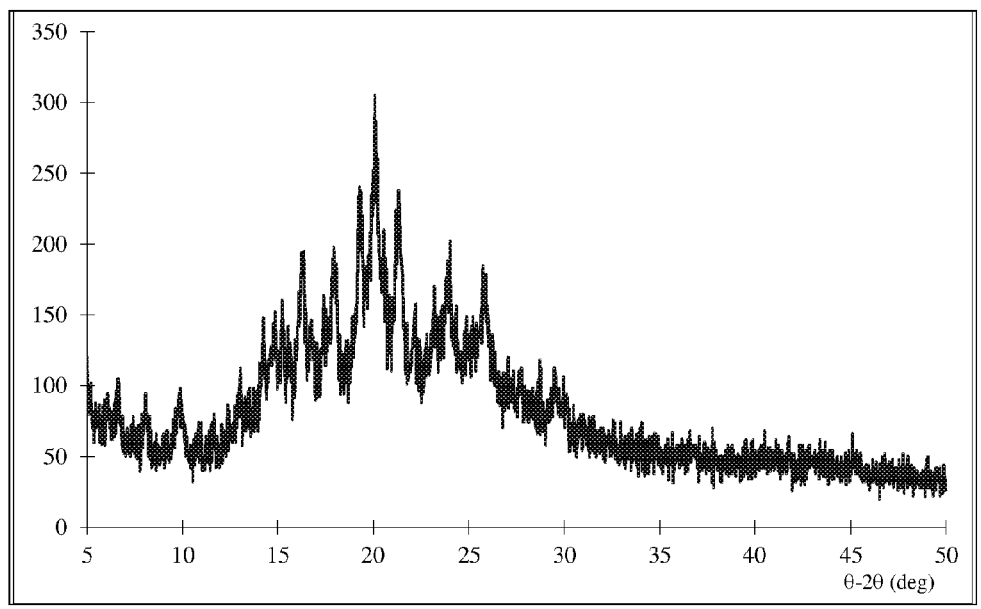
FIG. 1 is a graph illustrating the powder X-ray diffractometry of the commercial available (R)-(+)-verapamil HCl in accordance with one embodiment of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Unless defined otherwise, all technical and scientific terms used herein have the same meaning as commonly understood by one of the ordinary skill in the art to which the present disclosure belongs.

The singular forms "a", "and", and "the" are used herein to include plural referents unless the context clearly dictates otherwise. The term "about" as used herein generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, or reflection angles disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The present disclosure is aimed to obtain the crystalline of (R)-(+) verapamil HCl by a crystallization process, which in general, involves dissolving (R)-(+) verapamil HCl in a solvent until saturation, and cooling the saturated solution to precipitate the desired crystal therefrom. The obtained crystal is then subject to X-ray diffraction crystallographic analysis.

Accordingly, the crystals of the present disclosure respectively yield a characteristic powder X-ray diffraction pattern (XRD), and each crystal has a specific value of 2θ.

In a powder X-ray diffraction pattern, $I_{max}$ denotes the most intense peak in the powder X-ray diffraction chart measured in a powder sample of a crystal, whereas I denotes an intensity of each peak. The value of 2θ of the powder X-ray diffraction pattern can vary by approximately 0.1° to 0.5° with the state of the sample and measuring conditions. Because of properties of data of the powder X-ray diffraction pattern, general pattern is important for identifying the crystal form. Further, since a relative intensity can slightly vary with the growth direction of crystals, size of particles and/or measuring conditions, the intensity values in the XRD pattern should not be strictly interpreted.

The main objective of the present disclosure is to provide novel crystalline forms of (R)-(+) verapamil HCl.

To prepare novel crystalline forms of (R)-(+) verapamil HCl, (R)-(+) verapamil HCl is dissolved in suitable solvent(s) until a saturated solution is obtained; and the saturated solution is then cooled to form novel crystals therefrom.

According to embodiments of the present disclosure, at least 24 types of solvents have been tested, and among them, only 3 solvents meet the solubility criteria set forth in the examples of the present disclosure, and accordingly, 2 novel crystalline forms of (R)-(+) verapamil HCl are prepared.

Examples of solvent suitable for preparing novel crystalline forms of (R)-(+) verapamil HCl may be ethyl acetate, toluene, or a 1:1 volumetric mixture of 1,4-dioxane and heptane.

According to one embodiment, a novel crystalline of (R)-(+) verapamil HCl is prepared from a saturated ethyl acetate (EtOAc) solution. (R)-(+) verapamil HCl crystalizes from the saturated EtOAc solution is termed "form E crystal," which yields a powder X-ray diffraction pattern comprising characteristic peaks of 12.7°±0.1°, 18.7°±0.1°, 19.2°±0.1°, 20.2°±0.1°, and 21.2°±0.1° at reflection angles 2θ. According to a further example, the powder X-ray diffraction pattern of the form E crystalline of (R)-(+) verapamil hydrochloride further comprises characteristic peaks of 6.4°±0.1°, 8.3°±0.1°, 10.7°±0.1°, 15.5°±0.1°, 15.9°±0.1°, 17.5°±0.1°, 20.4°±0.1°, 23.9°±0.1°, 24.4°±0.1°, 25.4°±0.1°, 25.9°±0.1°, 27.7°±0.1°, 27.0°±0.1°, and 29.8°±0.1° at reflection angles 2θ. Specifically, it yields a powder X-ray diffraction pattern as substantially depicted in FIG. 2. Thermal analysis indicates a phase change occurred at an endothermic temperature from about 139±0.1° C. Hygroscopic analysis indicates the form E crystal may pick up 21% moisture at about 95% RH, as compared to about 30% of the non-crystalline form of verapamil hydrochloride.

According to another preferred embodiment, a novel crystalline of (R)-(+) verapamil HCl prepared from a saturated toluene solution. (R)-(+) verapamil HCl crystalizes from the saturated toluene solution is termed "form T crystal," which yields a powder X-ray diffraction pattern having characteristic peaks of a powder X-ray diffraction pattern comprising characteristic peaks of 8.5°±0.1°, 9.5°±0.1°, 17.6°±0.1°, 21.4°±0.1°, and 22.3°±0.1° at reflection angles 2θ. According to a further example, the powder X-ray diffraction pattern of form T crystalline of (R)-(+) verapamil hydrochloride further comprises characteristic peaks of 5.4°±0.1°, 9.6°±0.1°, 15.7°±0.1°, 17.1°±0.1°, 21.5°±0.1°, 21.6°±0.1°, 23.3°±0.1°, 24.6°±0.1° and 25.5°±0.1° at reflection angles 2θ. Specifically, it yields a powder X-ray diffraction pattern as substantially depicted in FIG. 3. Thermal analysis indicates a phase change occurred at an endothermic temperature from about 132±0.1° C. Hygroscopic analysis indicates the form T crystal may pick up about 23% moisture at about 95% RH, as compared to about 30% of the non-crystalline form of verapamil hydrochloride.

Impurity of the form E or T crystalline of (R)-(+) verapamil HCl is verified by high performance liquid chromatography (HPLC). According to embodiments of the present disclosure, the impurity level of the crystal of the present disclosure is reduced after each cooling and crystallizing step. Preferably, the individual impurity level of the crystal is less than 1.0%; more preferably, less than 0.5%; still more preferably, less than 0.1%. In the context of the present disclosure, the crystalline of the present disclosure having an impurity level less than 1.0% means that the crystal has less than 1.0% of other non-(R)-(+) verapamil HCl compounds; the crystalline of the present disclosure having an impurity level less than 0.5% means that the crystal has less than 0.5% of other non-(R)-(+) verapamil HCl compounds; and the crystalline of the present disclosure having an impurity level less than 0.1% means that the crystal has less than 0.1% of other non-(R)-(+) verapamil compound.

Any crystal thus obtained can be used as an active pharmaceutical ingredient of a medicine. Any of the crystal may be used alone or as a mixture of both forms.

In the present disclosure, the use of form E or T crystalline of (R)-(+) verapamil HCl is advantageous for handling and storage stability as compared with the case of using no crystal. Particularly, the form E or T crystalline of (R)-(+)-verapamil HCl is easily handled because of its crystal form, and the purification and drying effect is easily exerted; also, the crystal has improved storage stability and is useful as an active pharmaceutical ingredient of a medicine.

Specifically, each novel crystals of the present disclosure is useful as a medicament for treating diseases or conditions related to orexin receptors 1 and 2, somatostatin receptor 2, dopamine $D_{2L}$ receptor, sodium channel, or L-type and N-type calcium channels.

Examples for the diseases or conditions related to orexin receptors 1 and 2 include, but are not limited to, obesity, migraine, cluster headache, narcolepsy, Parkinson's disease, Alzheimer's disease, depression, addictions, anxiety, cancer, diabetes, insomnia, irritable bowel syndrome, neuropathic pain, pain, schizophrenia, sleep disorder, and Tourette syndrome. Examples for the disease or condition related to somatostatin receptor 2 include, but are not limited to, Crushing's syndrome, gonadotropinoma, gastrinoma, Zollinger-Ellison syndrome, hypersecretory diarrhea related to AIDS and other conditions, irritable bowel syndrome, pancreatitis, Crohn's disease, systemic sclerosis, thyroid cancer, psoriasis, hypotension, panic attacks, scleroderma, small bowel obstruction, gastroesophageal reflux, duodenogastric reflux, Grave's disease, polycystic ovary disease, upper gastrointestinal bleeding, pancreatic pseudocyst, pancreatic ascites, leukemia, meningioma, cancer cachexia, acromegaly, restenosis, hepatoma, lung cancer, melanoma, wasting, type 2 diabetes, Syndrome X, fibrosis, hyperlipidemia, hyperamylinemia, hyperprolactinemia, prolactinomas, cluster headache, depression, neuropathic pain and pain. Examples for the disease or condition related to dopamine $D_{2L}$ receptor include, but are not limited to, schizophrenia, anxiety, depression, migraine, pain, Parkinson's disease, addiction and Tourette syndrome. Examples for the disease or condition related to sodium channel include, but are not limited to, atrial fibrillation, ventricular fibrillation, long QT syndrome, and hyperkalaemic periodic paralysis. Examples for the disease or condition related to L- and N-type calcium channels include, but are not limited to, hypokalaemic periodic paralysis, episodic ataxia type 2, and familia hemiplegic migraine.

Accordingly, each crystal of (R)-(+) verapamil HCl or a solvent thereof of the present disclosure may constitute pharmaceutical compositions with pharmaceutical acceptable carriers, and can be administered to a subject orally or parenterally in various dosage forms. Parenteral administration includes, for example, administration by intraveneous, subcutaneous, intramuscular, transdermal, intrarectal, transnasal, and instillation methods.

The dosage form of the pharmaceutical composition for oral administration includes, for example, tablets, pills, granules, powders, solutions, suspensions, syrups or capsules. As a method of producing a tablet, a pill, granule or powder, it can be formed by conventional techniques using a pharmaceutically acceptable carrier such as excipient, binder, or disintegrant and etc. As to the form of a solution, suspension or syrup, it can be produced by conventional techniques using glycerol esters, alcohols, water or vegetable oils, and etc. The form of capsule can be produced by filling a capsule made of gelatin with the granule, powder or a solution prepared as described above. Among the agents for parenteral administration, in the case of intravenous, subcutaneous or intramuscular administration, it can be administered as injection. An injection can be prepared by dissolving the crystalline of the present disclosure in water soluble solution such as physiological saline, or water insoluble solution consisting of organic esters such as propylene glycol, polyethylene glycol, or vegetable oils (e.g., sesame oil). In the case of transdermal administration, for example, a dosage form as an ointment or a cream can be employed. The ointment can be produced by mixing the crystal of the present disclosure with fats or oils and etc; and the cream can be produced by mixing the crystal of the present disclosure with emulsifiers. In the case of rectal administration, it may be in the form of suppository using a gelatin soft capsule. In the case of transdermal administration, it may be in a form of a liquid or a powdery formulation. In a liquid formulation, water, salt solution, phosphate buffer, acetate buffer and etc may be used as a base; it may also contain surfactants, antioxidants, stabilizers, preservatives or tackifiers. In a powdery formulation, it may contain water-absorbing materials such as water-soluble polyacrylates, cellulose low-alkyl esters, polyethylene glycol polyvinyl pyrrolidone, amylase and etc, and non-water absorbing materials such as cellulose, starches, gums, vegetable oils or cross-linked polymers. Further, antioxidants, colorants, preservatives may be added to the powdery formulation. The liquid or powdery formulation may be administered by use of a spray apparatus. In case of inhalation through nose or mouth, a solution or suspension containing the crystal of the present disclosure and a pharmaceutical excipient generally accepted for this purpose is inhaled through an inhalant aerosol spray. Alternatively, the crystal of the present disclosure in the form of a powder may be administered through inhalator that allows direct contact of the powder with the lung. To these formulations, if necessary, pharmaceutical acceptable carriers such as isotonic agents, preservatives, dispersions, or stabilizers may be added. Further, if necessary, these formulations may be sterilized by filtration, or by treatment with heat or irradiation.

The pharmaceutical composition or medicament comprising an effective amount of the crystalline of the present disclosure is suitable for treating diseases or conditions related to orexin receptors 1 and 2, somatostatin receptor 2, dopamine $D_{2L}$ receptor, sodium channel, and L- and N-type calcium channels, such as obesity, migraine, cluster headache, narcolepsy, Parkinson's disease, Alzheimer's disease, depression, addictions, anxiety, cancer, diabetes, insomnia, irritable bowel syndrome, neuropathic pain, pain, schizophrenia, sleep disorder, Tourette syndrome, Crushing's syndrome, gonadotropinoma, gastrinoma, Zollinger-Ellison syndrome, hypersecretory diarrhea related to AIDS and other conditions, pancreatitis, Crohn's disease, systemic sclerosis, psoriasis, hypotension, panic attacks, scleroderma, small bowel obstruction, gastroesophageal reflux, duodeno-gastric reflux, Grave's disease, polycystic ovary disease, upper gastrointestinal bleeding, pancreatic pseudocyst, pancreatic ascites, leukemia, meningioma, cancer cachexia, acromegaly, restenosis, hepatoma, lung cancer, melanoma, wasting, type 2 diabetes, Syndrome X, fibrosis, hyperlipidemia, hyperamylinemia, hyperprolactinemia, prolactinomas, cluster headache, depression, anxiety, addiction, atrial fibrillation, ventricular fibrillation, long QT syndrome, hyperkalaemic periodic paralysis, hypokalaemic periodic paralysis, episodic ataxia type 2, and familia hemiplegic migraine.

The effective amount of the crystal of the present disclosure suitable for treating any of the afore-mentioned conditions varies with the route of administration, or condition, age, sex, or weight of the subject receiving the treatment. In general, the crystal of the present disclosure is administered to the subject at least once a week, such as 1, 2, or 3 times per week. The effective amount is about 10-2,000 mg/week, preferably about 20-1,800 mg/week in the case of oral administration; whereas it is about 1-1,000 mg/week, preferably about 5-500 mg/week in the case of intravenous, intramuscular, subcutaneous, transdermal, transnasal, intrarectal, or inhalation.

The present disclosure will now be described in further detail with reference to the following examples. However, it should be understood that the present disclosure is not limited to the specified examples.

EXAMPLES

Materials and Methods
Materials.
(R)-(+)-verapamil HCl was purchased from Syn-Tech Chem. & Pharma Co. Ltd (Tainan, Taiwan, R.O.C.)
Crystallization.
Crystallization was carried out by slow and/or fast cooling from a hot saturated solution. In general, about 30 mg (R)-(+)-verapamil HCl was dissolved in the least volume of indicated solvents, including those listed in the following Table 1, and others, such as N,N-dimethylacetamide, acetic acid, and etc, at 53-70° C. until all powders were completely dissolved. The temperature varied with the choice of solvent, in the case when EtOAc was used, about 30 mg of (R)-(+)-verapamil HCl powders were dissolved in the least possible volume of EtOAc at 53-60° C.; in the case when a mixture of 1,4-dioxane/heptane (1:1) was used, the powders were dissolved at 60° C.; whereas if toluene was used, then the powders were dissolved in least amount of toluene and heated to about 70° C. till the powders were completely dissolved. The solution was then placed in two different vials and subject to fast and slow cooling, respectively. For slow cooling, the vial was left to cool down to room temperature (about 25° C.); as to fast cooling, the vial was immediately placed in an iced bath to cool to about 4° C. Both solutions, either in the fast or slow cooling, were let stand for no more than 3 days.

Thermal Analysis.
The crystal was subject to differential scanning calorimetry (DSC) analysis over the range of 30° C./300° C. with a gradient of 10° C./min under nitrogen purge, and the presence or absence of endotherm peaks was observed.

Similarly, the crystal was also subject to thermogravimetric (TGA) analysis over the range of 30° C./350° C. with a gradient of 10° C./min under nitrogen purge; and weight loss, decomposition, and phase transition of the crystal were observed.

The melting point of the crystal was determined using a capillary method (e.g., Thomas-Hoover or the Mel-Temp apparatus). In general, a few crystals were placed in a thin-walled capillary tube about 10-15 cm in length, and about 1 mm in inside diameter, and closed at one end. The capillary, which contained the sample, and a thermometer were then suspended so that they were heated slowly and evenly. The temperature range over which the sample was observed to melt was taken as the melting point.

X-ray Powder Diffractometry.
X-ray diffraction patterns were obtained on D2 phaser X-ray diffractometer system (Bruker AXS Gmbh, Germany). Samples were scanned in continuous mode from 5-50° (2θ) with step size of 5θ/min on a spinning stage at 30 kV and 10 mA with Cu Kα radiation (1.54056 Å). The incident beam path was equipped with a 1 mm divergence slit and 1 mm air scattering screen. The diffracted beam was equipped with Ni-filter. Detection was accomplished with a Lynxeye (2.5) detector (Bruker AXS).

Hygroscopicity.
Hygroscopicity was determined by dynamic vapor sorption (DVS) performed on the DVS Advantage (Surface Measurement Systems Ltd., London) DVS is a technique that measures how quickly and how much of a solvent (e.g., water or an organic solvent) being absorbed by a sample. Measurements were taken from 0 to 95% RH at 25° C. with 5% RH per step with equilibration set to dm/dt+0.002%/min for 5 min or 120 min/step. All samples reached equilibration at each step before the 120 min maximum set point was reached.

Storage Stability.
Crystal samples were placed in an environment of (a) 40° C./75% RH, open vial; (b) 50° C., airtight container; and (c) 4,500 LUX, respectively, for 1, 7 and 21 days, and thereafter subjected to high performance liquid chromatography (HPLC) to determine the level of impurity.

Example 1 Preparation of New Crystal Forms of (R)-(+)-verapamil HCl

In this example, the commercial available (R)-(+)-verapamil HCl was subject to polymorph screening so as to identify new crystal forms of (R)-(+)-verapamil HCl.

1.1 Polymorph Screening
The commercial available (R)-(+)-verapamil HCl was dissolved in various types of solvents as indicated in Table 1, and solubility was visually assessed.

TABLE 1

Solubility of (R)-(+)-verapamil HCl in various types of solvent

| # | Solvent | Solubility (mg/ml) |
|---|---------|--------------------|
| 1 | acetone | >20 |
| 2 | ACN | >20 |
| 3 | DMSO | >20 |
| 4 | H$_2$O | >20 |
| 5 | n-propanol | >20 |
| 6 | MEK | >20 |
| 7 | 1,4-dioxane | >20 |
| 8 | EG | >20 |
| 9 | H$_2$O/IPA 1:1 | >20 |
| 10 | H$_2$O/THF (1:1) | >20 |

TABLE 1-continued

Solubility of (R)-(+)-verapamil HCl in various types of solvent

| # | Solvent | Solubility (mg/ml) |
|---|---------|--------------------|
| 11 | H₂O/acetone (1:1) | >20 |
| 12 | EtOH/DCM (1:1) | >20 |
| 13 | EtOH/heptane (1:1) | >20 |
| 14 | toluene/MetOH (1:1) | >20 |
| 15 | DCM | 15-19 |
| 16 | IPA | 15-19 |
| 17 | DMF | 15-19 |
| 18 | THF | 15-19 |
| 19 | EtOH/MEK (1:1) | 15-19 |
| 20 | 1-butanol | 15-19 |
| 21 | EtOAc | ~5 |
| 22 | 1,4-dioxane/heptane (1:1) | ~5 |
| 23 | toluene | ~1 |
| 24 | heptane | <1 |

ACN: Acetonitrile;
DCM: Dichloromethane;
DMF: dimethylformamide;
DMSO: dimethyl sulfoxide;
EG: ethylene glycol;
MetOH: methanol;
IPA: isopropanol;
EtOAc: ethyl acetate;
MEK: methyl ethyl ketone;
THF: tetrahydrofuran.

Among the 24 types of solvents that were tested, the solubility of (R)-(+)-verapamil HCl differed from one solvent to another, it varied from "quite soluble," "soluble," "soluble to just a minor extend," to "insoluble." Specifically, (R)-(+)-verapamil HCl was found to be quite soluble in water, acetone, DMSO, MEK, ACN, n-propanol, 1,4-dioxane, ethylene glycol, H₂O/IPA (1:1), H₂O/THF (1:1), H₂O/acetone (1:1), EtOH/DCM (1:1), EtOH/heptane (1:1), and toluene/MetOH (1:1); soluble in DCM, DMF, IPA, THF, EtOH/MEK (1:1), 1-butanol; soluble to just a minor extent in EtOAc, toluene, 1,4-dioxane/heptane (1:1); and insoluble in heptane. Thus, EtOAc, toluene, and 1,4-dioxane/heptane (1:1) were chosen as the solvents for subsequent crystallization.

1.2 Preparation of Form E Crystal (R)-(+)-verapamil HCl was dissolved in EtOAc and crystallized in accordance with the procedures described in "Materials and Methods" section.

The crystal was subject to X-ray diffraction (XRD) and thermal analysis, and was termed "form E."

Figure 2:
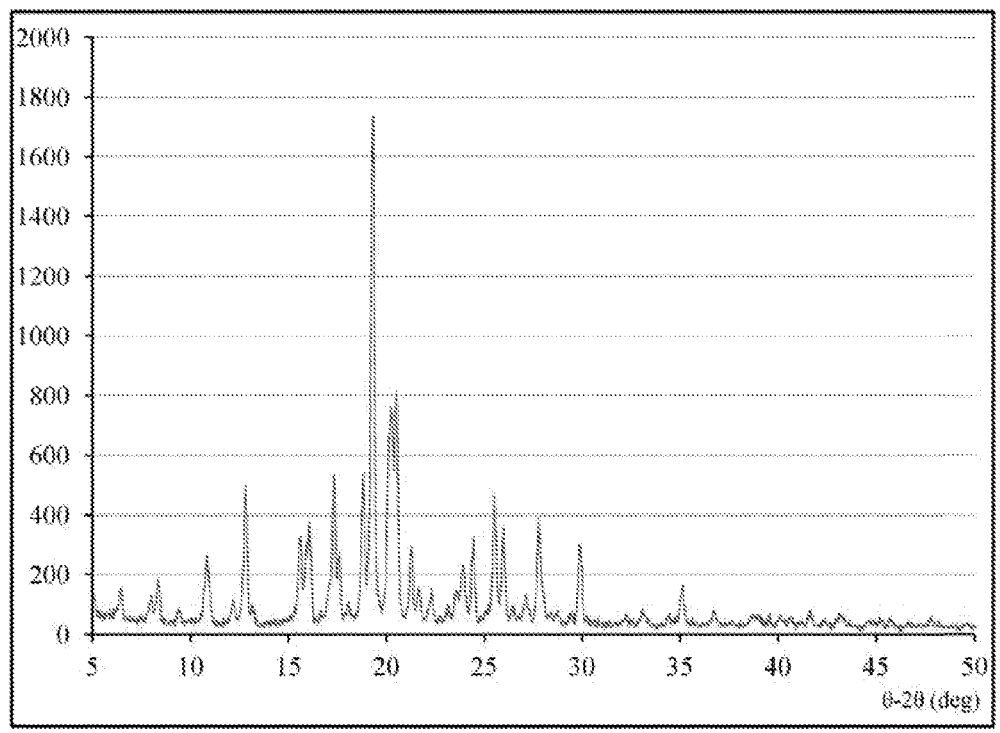
FIG. 2 is a graph illustrating the powder X-ray diffractometry of the Form E crystal of (R)-(+)-verapamil HCl in accordance with one embodiment of the present disclosure.

FIG. 2 illustrates the X-ray diffraction pattern of form E crystal, in which major diffraction peaks were observed at approximately 12.7°±0.1°, 18.7°±0.1°, 19.2°±0.1°, 20.2°±0.1°, and 21.2°±0.1° at reflection angles 2θ; minor diffraction peaks were observed at approximately 6.4°±0.1°, 8.3°±0.1°, 10.7°±0.1°, 15.5°±0.1°, 15.9°±0.1°, 17.5°±0.1°, 20.4°±0.1°, 23.9°±0.1°, 24.4°±0.1°, 25.4°±0.1°, 25.9°±0.1°, 27.0°±0.1°, 27.7°±0.1°, and 29.8°±0.1° at reflection angles 2θ. The XRD pattern of form E crystal of (R)-(+)-verapamil HCl (FIG. 2) appeared to be quite different from that of the control (i.e., the commercial (R)-(+)-verapamil HCl, FIG. 1).

Figure 4:
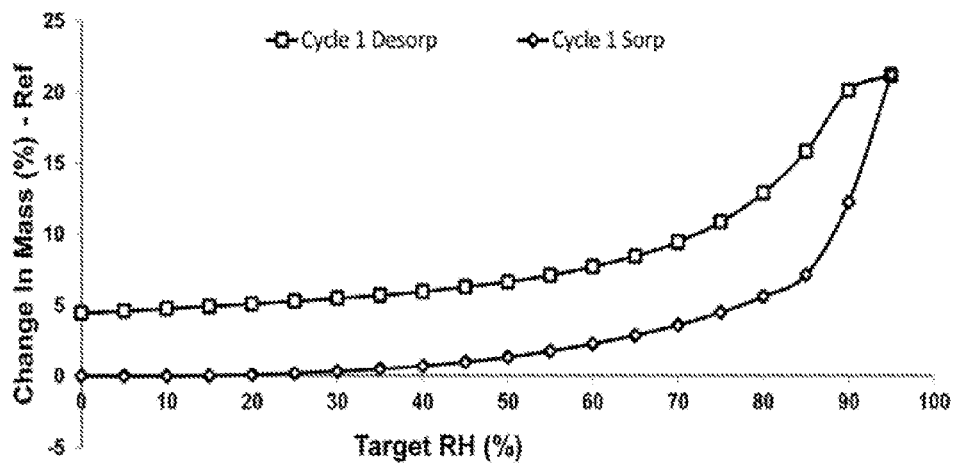
FIG. 4 is a graph illustrating the moisture sorption and desorption of the Form E crystal of (R)-(+)-verapamil HCl in accordance with one embodiment of the present disclosure.

As to thermal analysis, DSC analysis indicated a phase changed occurred at endothermic temperature at about 139±0.1° C. (see FIG. 4). TGA analysis indicated a weight loss of about 1.70% before 150° C. We thus concluded that form E was a new crystal form of (R)-(+)-verapamil HCl.

1.3 Preparation of Form T Crystal (R)-(+)-verapamil HCl was dissolved in toluene and crystallized in accordance with the procedures described in "Materials and Methods" section.

The crystal was subject to X-ray diffraction (XRD) and thermal analysis, and was termed "form T."

Figure 3:
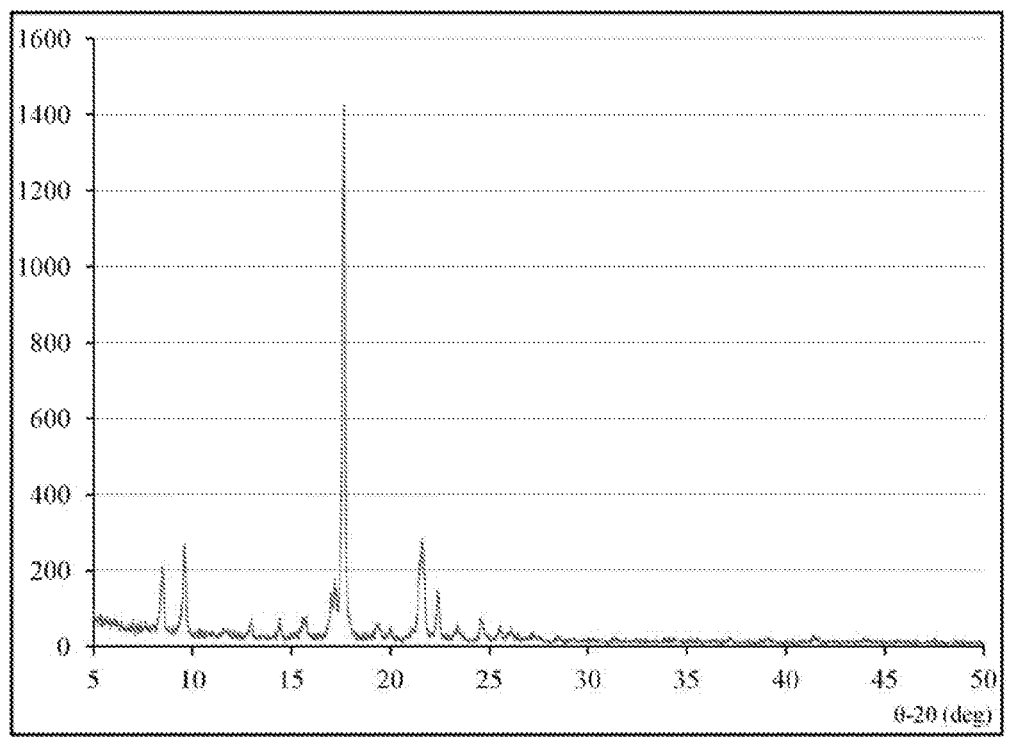
FIG. 3 is a graph illustrating the powder X-ray diffractometry of the Form T crystal of (R)-(+)-verapamil HCl in accordance with one embodiment of the present disclosure.

FIG. 3 illustrates the X-ray diffraction pattern of form T crystal, in which major diffraction peaks were observed at approximately 8.5°±0.1°, 9.5°±0.1°, 17.6°±0.1°, 21.4°±0.1°, and 22.3°±0.1° at reflection angles 2θ; and minor diffraction peaks were observed at approximately 5.4°±0.1°, 9.6°±0.1°, 15.7°±0.1°, 17.1°±0.1°, 21.5°±0.1°, 21.6°±0.1°, 23.3°±0.1°, 24.6°±0.1° and 25.5°±0.1° at reflection angles 2θ. The XRD pattern of form T crystal of (R)-(+)-verapamil HCl (FIG. 3) appeared to be quite different from that of the control (i.e., the commercial (R)-(+)-verapamil HCl, FIG. 1).

Figure 5:
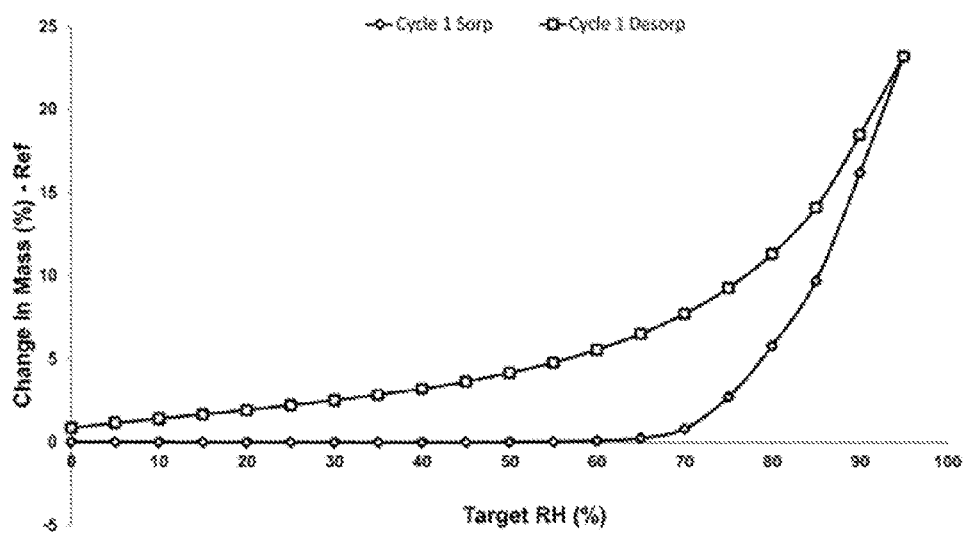
FIG. 5 is a graph illustrating the moisture sorption and desorption of the Form T crystal of (R)-(+)-verapamil HCl in accordance with one embodiment of the present disclosure.

As to thermal analysis, DSC analysis indicated a phase changed occurred at endothermic temperature from about 132±0.1° C. (see FIG. 5). TGA analysis indicated a weight loss of about 3.63% before 150° C. We thus concluded that form T was also a new crystal form of (R)-(+)-verapamil HCl.

Example 2 Characterization of the Crystals of Example 1.2 and 1.3

2.1 Hygroscopicity Analysis

The form E crystal of Example 1.2 and form T crystal of example 1.3 were respectively subject to hygroscopicity analysis in accordance with procedures described in "Materials and Methods" section.

The results indicated that form E and form T crystals respectively picked up about 21% and 23% moisture at 95% RH.

2.2 Storage Stability of the Crystals of Example 1.2 and 1.3

The form E crystal of Example 1.2 and form T crystal of example 1.3 were respectively placed in containers and stored in the designated conditions as described in the "Materials and Methods" section, and thereafter subjected to HPLC analysis to determine the level of impurity. Results are summarized in Table 2.

TABLE 2

Storage Stability of Crystals of Example 1.2 and 1.3

| | | Total impurities (%) | Impurity % | |
|---|---|---|---|---|
| | Storage Conditions | | Unknown 1 | Unknown 2 |
| (R)-Verapamil HCl powder (non-crystal form) | 0 day | 0.02 | 0.012 | 0.005 |
| | 40° C./RH75% 1 week | 0.02 | 0.014 | 0.006 |
| | 50° C. 1 week | 0.03 | 0.019 | 0.009 |
| | light 1 week | 0.03 | 0.017 | 0.016 |
| | 40° C./RH75%/3 weeks | 0.03 | 0.022 | 0.011 |
| | 50° C./3 weeks | 0.05 | 0.032 | 0.017 |
| | Light/3 weeks | 0.09 | 0.036 | 0.050 |
| Form E | 0 day | 0.03 | 0.019 | 0.015 |
| | 40° C./RH75% 1 week | 0.02 | 0.014 | 0.009 |
| | 50° C. 1 week | 0.04 | 0.023 | 0.016 |
| | light 1 week | 0.03 | 0.007 | 0.020 |
| | 40° C./RH75%/3 weeks | 0.01 | 0.001 | 0.011 |
| | 50° C./3 weeks | 0.04 | 0.026 | 0.014 |
| | Light/3 weeks | 0.05 | 0.017 | 0.036 |

TABLE 2-continued

Storage Stability of Crystals of Example 1.2 and 1.3

| | Storage Conditions | Total impurities (%) | Impurity % Unknown 1 | Impurity % Unknown 2 |
|---|---|---|---|---|
| Form T | 0 day | 0.02 | 0.01 | 0.008 |
| | 40° C./RH75%/1 week | 0.00 | 0.001 | Not detected |
| | 50° C./1 week | 0.00 | 0.004 | Not detected |
| | light/1 week | 0.01 | 0.006 | 0.003 |
| | 40° C./RH75%/3 weeks | 0.00 | 0.001 | Not detected |
| | 50° C./3 weeks | 0.01 | 0.008 | 0.001 |
| | Light/3 weeks | 0.03 | 0.010 | 0.015 |

As a result, no change was observed in comparison with the state before storage for either form E or T crystal. Among various storage conditions tested, the condition for storage under 40° C., 75% RH for 3 weeks, both form E and form T crystals were more stable than the control verapamil powder.

It will be understood that the above description of embodiments is given by way of example only and that various modifications may be made by those with ordinary skill in the art. The above specification, examples, and data provide a complete description of the structure and use of exemplary embodiments of the disclosure. Although various embodiments of the disclosure have been described above with a certain degree of particularity, or with reference to one or more individual embodiments, those with ordinary skill in the art could make numerous alterations to the disclosed embodiments without departing from the spirit or scope of this disclosure.

What is claimed is:

1. A form T crystalline of (R)-(+)-verapamil hydrochloride comprising a powder X-ray diffraction pattern comprising characteristic peaks of 8.5°±0.1°, 9.5°±0.1°, 17.6°±0.1°, 21.4°±0.1°, and 22.3°±0.1° at reflection angles 2θ.

2. The form T crystalline of (R)-(+)-verapamil hydrochloride of claim 1, further comprising characteristic peaks of 5.4°±0.1°, 9.6°±0.1°, 15.7°±0.1°, 17.1°±0.1°, 21.5°±0.1°, 21.6°±0.1°, 23.3°±0.1°, 24.6°±0.1° and 25.5°±0.1° at reflection angles 2θ.

3. The form T crystalline of (R)-(+)-verapamil hydrochloride of claim 2, wherein the powder X-ray diffraction pattern is substantially as depicted in FIG. 3.

4. The form T crystalline of (R)-(+)-verapamil hydrochloride of claim 1, wherein, as measured by DSC, the form T crystalline has an endothermic peak at about 132±0.1° C.

5. The form T crystalline of (R)-(+)-verapamil hydrochloride of claim 1, wherein the crystal has a water content of about 0% (wt %) at 3% RH, and about 23% (wt %) at 95% RH.

* * * * *